United States Patent
Henderson

(10) Patent No.: US 10,195,054 B1
(45) Date of Patent: Feb. 5, 2019

(54) ACETABULAR CUP ALIGNMENT SYSTEM

(71) Applicant: Dartmouth-Hitchcock Clinic, Lebanon, NH (US)

(72) Inventor: Eric R. Henderson, Lebanon, NH (US)

(73) Assignee: Dartmouth-Hitchcock Clinic, Lebanon, NH (US)

(*) Notice: Subject to any disclaimer, the term of this patent is extended or adjusted under 35 U.S.C. 154(b) by 576 days.

(21) Appl. No.: 14/956,317

(22) Filed: Dec. 1, 2015

Related U.S. Application Data

(60) Provisional application No. 62/086,510, filed on Dec. 2, 2014.

(51) Int. Cl.
| | |
|---|---|
| *A61B 17/58* | (2006.01) |
| *A61B 17/60* | (2006.01) |
| *A61F 2/00* | (2006.01) |
| *A61F 2/46* | (2006.01) |
| *A61B 34/20* | (2016.01) |

(52) U.S. Cl.
CPC ............ *A61F 2/4609* (2013.01); *A61B 34/20* (2016.02); *A61B 2034/207* (2016.02); *A61F 2002/4632* (2013.01)

(58) Field of Classification Search
None
See application file for complete search history.

(56) References Cited

U.S. PATENT DOCUMENTS

| | | |
|---|---|---|
| 5,141,512 A | 8/1992 | Farmer et al. |
| 6,214,014 B1 | 4/2001 | McGann |
| 6,743,235 B2 | 6/2004 | Subba Rao |
| 2006/0184177 A1 | 8/2006 | Echeverri |
| 2009/0099665 A1 | 4/2009 | Taylor et al. |
| 2011/0152871 A1 | 6/2011 | Park et al. |
| 2011/0190775 A1 | 8/2011 | Ure |
| 2012/0226283 A1 | 9/2012 | Meridew et al. |
| 2012/0283599 A1 | 11/2012 | Borja |
| 2013/0053856 A1 | 2/2013 | Penenberg |
| 2013/0053857 A1 | 2/2013 | Penenberg |

OTHER PUBLICATIONS

Jeffers, et al., "Laser Guided Instrumentation for Acetabular Placement in Hip Arthroplasty", "ISTA 2008", Oct. 1, 2008, p. 121 Publisher: ISTA, Published in: US.

*Primary Examiner* — Sameh Boles
(74) *Attorney, Agent, or Firm* — Loginov & Associates, PLLC; William A. Loginov

(57) ABSTRACT

A system for an acetabular cup alignment includes a mounting element; a first pivot; a first support arm, the first support arm being axially rotatable relative to the first pivot; a second pivot; a second support arm that is attached to the second pivot at an end, the second support arm being axially rotatable relative to the second pivot; a third pivot; a third support arm that is attached to the third pivot at an end, the third support arm being axially rotatable relative to the third pivot; a red laser housing that is provided with at least one red laser light emitter, the red laser housing being attached to the second pivot; and a green laser housing that is provided with at least one green laser light emitter, the green laser housing being attached to the third support arm.

11 Claims, 4 Drawing Sheets

ACETABULAR CUP ALIGNMENT SYSTEM

RELATED APPLICATION

This application claims the benefit of U.S. Provisional Application Ser. No. 62/086,510, entitled ACETABULAR CUP ALIGNMENT SYSTEM, filed Dec. 2, 2014, by Eric R. Henderson, the teachings of which are incorporated herein by reference.

FIELD OF THE INVENTION

This invention is in the field of medical devices, and more particularly devices for aligning surgical tools.

BACKGROUND OF THE INVENTION

The acetabulum is a concave surface of the pelvis. The head of the femur meets with the pelvis at the acetabulum, forming the hip joint. There are three bones of the os coxae (hip bone) that come together to form the acetabulum. Contributing a little more than two-fifths of the structure is the ischium, which provides lower and side boundaries to the acetabulum. The ilium forms the upper boundary, providing a little less than two-fifths of the structure of the acetabulum. The rest is formed by the pubis, near the midline. It is bounded by a prominent uneven rim, which is thick and strong above, and serves for the attachment of the acetabular labrum, which reduces its opening, and deepens the surface for formation of the hip joint. At the lower part of the acetabulum is the acetabular notch, which is continuous with a circular depression, the acetabular fossa, at the bottom of the cavity of the acetabulum. The rest of the acetabulum is formed by a curved, crescent-moon shaped surface, the lunate surface, where the joint is made with the head of the femur. The acetabulum is also home to the acetabular notch, an attachment site for the ligamentum teres, a triangular, somewhat flattened band implanted by its apex into the antero-superior part of the fovea capitis femoris. The notch is converted into a foramen by the transverse acetabular ligament; through the foramen nutrient vessels and nerves enter the joint. This is what holds the head of the femur securely in the acetabulum.

The well-fitting surfaces of the femoral head and acetabulum, which face each other, are lined with a layer of slippery tissue called articular cartilage, which is lubricated by a thin film of synovial fluid. Friction inside a normal hip is less than one-tenth that of ice gliding on ice. Dislocation is the most common complication of hip replacement surgery. At surgery the femoral head is taken out of the socket, hip implants are placed and the hip put back into proper position. It takes eight to twelve weeks for the soft tissues injured or cut during surgery to heal. During this period, the hip ball can come out of the socket. The chance of this is diminished if less tissue is cut, if the tissue cut is repaired and if large diameter head balls are used. Doing the surgery from an anterior approach seems to lower dislocation rates when small diameter heads are used, but the benefit has not been shown when compared to modern posterior incisions with the use of larger diameter heads.

The acetabular cup is the component which is placed into the acetabulum (hip socket). Cartilage and bone are removed from the acetabulum and the acetabular cup is attached using friction or cement. Some acetabular cups are one piece, while others are modular. One piece (monobloc) shells are either UHMWPE (ultra-high-molecular-weight polyethylene) or metal, they have their articular surface machined on the inside surface of the cup and do not rely on a locking mechanism to hold a liner in place. A monobloc polyethylene cup is cemented in place while a metal cup is held in place by a metal coating on the outside of the cup. Modular cups consist of two pieces, a shell and liner. The shell is made of metal, the outside has a porous coating while the inside contains a locking mechanism designed to accept a liner. Two types of porous coating used to form a friction fit are sintered beads or a foam metal design to mimic the trabeculae of cancellous bone. Additional fixation is achieved as bone grows onto or into the porous coating. Screws can be used to lag the shell to the bone providing even more fixation. Polyethylene liners are placed into the shell and connected by a rim locking mechanism, ceramic and metal liners are attached with a Morse taper.

FIG. 1 depicts a conventional impactor, according to the background art. The exemplary impactor 100 is depicted as ready for impaction of a replacement acetabular cup 102. The acetabular cup 102 is temporarily attached to the cup engaging element 104 located at a first end 106 of the impactor body 108. The second end 110 is comprised of a handle 112 and an impaction anvil 114. The control elements of the impactor include a rotating outer end rod 120 with attached operating knob 122 and a rack 124 for changing the orientation of the rotating outer end rod 120 to maneuver the cup engaging element 104. Control lever 126 and crank 128 are additional control elements. Once the impactor 100 is aligned, the operator strikes the impactor anvil 114 with a hammer (not shown), driving the cup 102 into the hip and the cup 100 is securely seated.

Acetabular cup procedures require proper alignment for optimal outcome. Correct placement of the acetabular cup in total hip arthroplasty is a crucial step to achieve a satisfactory result and remains a challenge with free-hand techniques. Indeed, malpositioning can induce early loosening, high wear and postoperative dislocation. Various investigators have demonstrated that conventional free-hand positioning can result in a high percentage of unacceptable acetabular cup placements. Manual digitization can potentially cause measurement error which, in turn, can result in excessive tilt of the cup in the frontal plane. This is particularly problematic in obese patients where excess soft tissue can completely obscure bony landmarks.

Commercially available mechanical guides for alignment of the cup include a certain level of subjectivity on the part of the surgeon regarding alignment. Use of mechanical acetabular guides for intraoperative alignment leads to variations between the actual and desired implant orientation. These variations lead to a need for corrective procedures to revise the alignment of the implants.

It would be desirable to provide a system for alignment that relies on an objective system, minimizes subjectivity and thereby optimizes a beneficial outcome for the patient.

SUMMARY OF THE INVENTION

The present invention overcomes the disabilities of the prior art by providing a system for aligning the acetabulum using laser emitted light. A system for an acetabular cup alignment system includes a mounting element; a first pivot that is provided with an upper pivot portion and a lower pivot portion, the first pivot being attached to the mounting element; a first support arm that is attached to the first pivot at an end, the first support arm being axially rotatable relative to the first pivot; a second pivot that is provided with an upper pivot portion and a lower pivot portion, the second pivot being attached to an end of the first support arm; a second support arm that is attached to the second pivot at an end, the second support arm being axially rotatable relative to the second pivot; a third pivot that is provided with an upper pivot portion and a lower pivot portion, the third pivot being attached to an end of the second support arm; a third support arm that is attached to the third pivot at an end, the third support arm being axially rotatable relative to the third pivot; a red laser housing that is provided with at least one red laser light emitter, the red laser housing being attached to the second pivot; and a green laser housing that is provided with at least one green laser light emitter, the green laser housing being attached to the third support arm. The mounting element can be a ceiling mount. The red laser light housing has a handle for aligning and positioning the red laser light emitter. The red laser light housing has a first longitudinal aperture, a central circular aperture and a second longitudinal aperture. The first and second longitudinal apertures emit a linear beam of light. The central circular light aperture emits a central point beam of light. The green laser light housing has a handle for aligning and positioning the green laser light emitter. The green laser light housing has a first longitudinal aperture, a central circular aperture and a second longitudinal aperture. The first and second longitudinal apertures emit a linear beam of light. The central circular light aperture emits a central point beam of light. The third support arm has a track for the green laser housing that provides for lateral movement of the green laser housing. A method for aligning an acetabular cup using an acetabular cup alignment system is comprised of the steps of positioning the patient acetabulum; taking a pre-operative x-ray image to judge pelvic tilt of the patient; evaluating the correctness of the pelvic tilt; re-positioning the patient acetabulum and re-taking pre-operative x-ray images until the pelvic tilt is correct; positioning the red center point laser directly over the acetabulum; recording the inclination of the acetabulum; positioning the green point laser so that the green center point laser references the center of the acetabulum by moving the green laser housing closer or further from the red laser housing and radially about the red laser housing; aligning the green point laser with the center of the cup engaging element of the impactor to provide accurate referencing of the acetabular component; and beginning the impaction of the acetabular cup.

BRIEF DESCRIPTION OF THE DRAWINGS

The invention description below refers to the accompanying drawings, of which.

DETAILED DESCRIPTION

Figure 1:
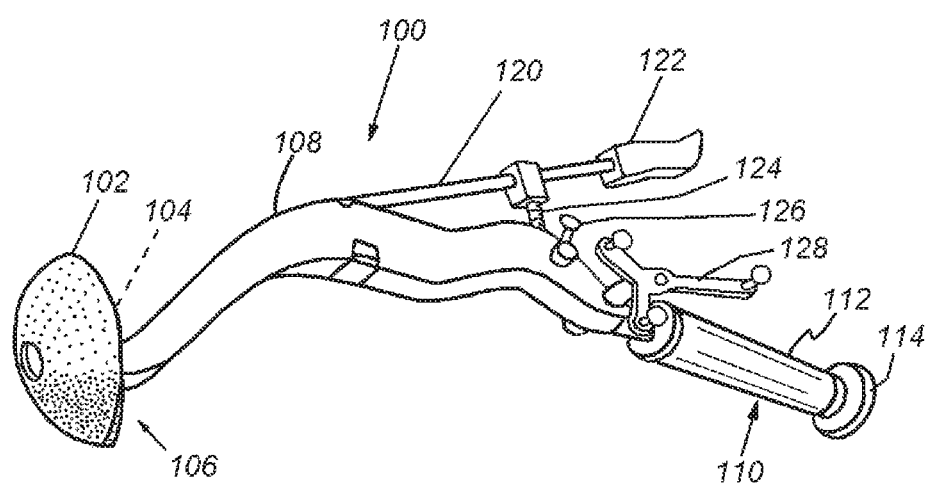
FIG. 1, already described, is a perspective view of an exemplary impactor, according to the background art.
Figure 2:
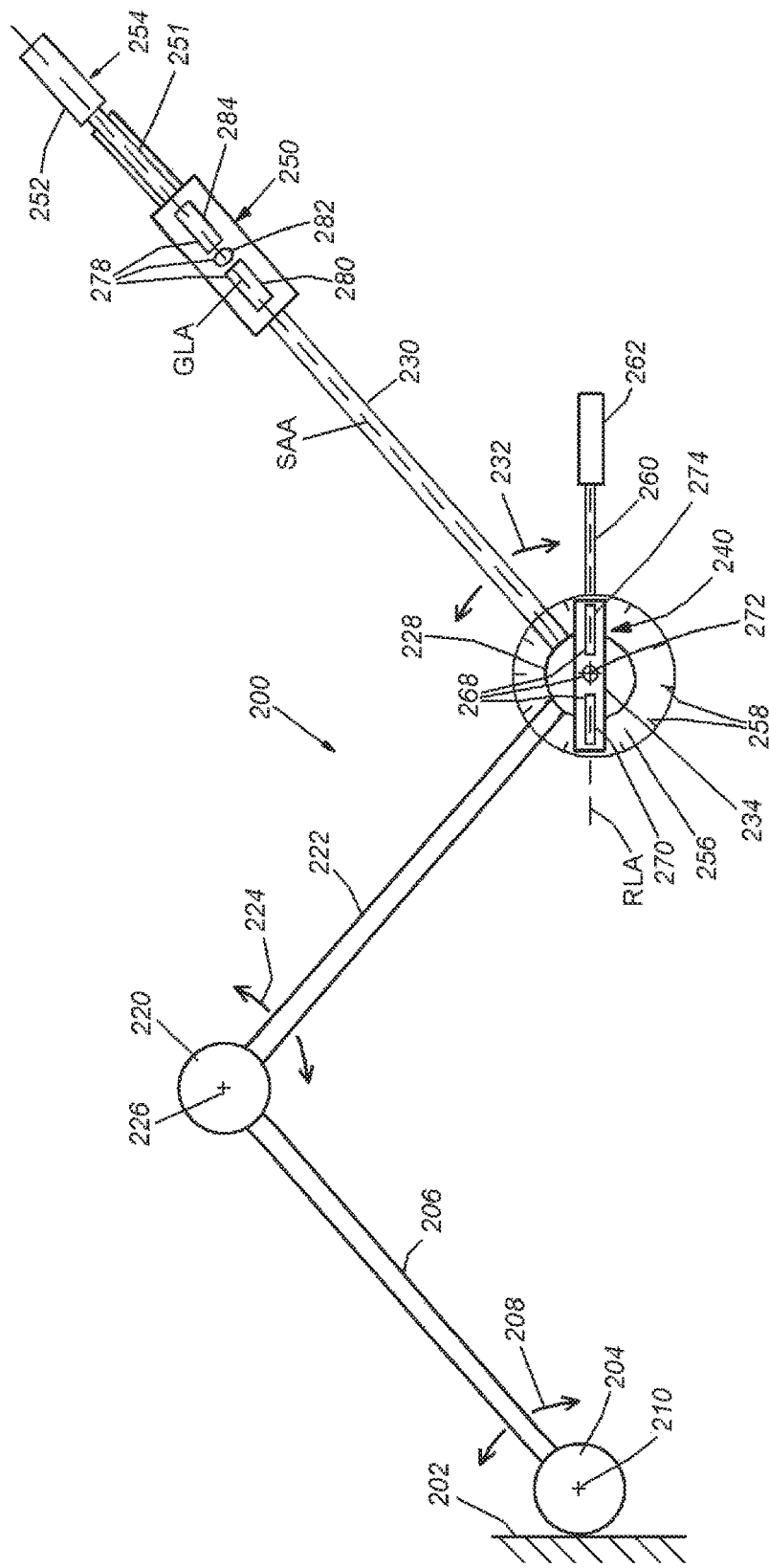
FIG. 2 is a schematic view of a system for alignment, according to an illustrative embodiment.

A system for alignment 200 is shown in FIG. 2. An illustrative system is comprised of a plurality of support arms connected to each other at pivots and provided with various laser housings. The alignment system 200 is mounted by a mounting element 202 to a ceiling of a room for medical procedures in an illustrative embodiment. In other embodiments, the mounting element for the alignment system 200 is attached to a wall, support member or other appropriate mounting structure. A first pivot 204 is connected to the mounting element 202. A first support arm 206 is connected to the first pivot 204 at one end and is moveable through an arc of movement 208 around the first pivot center 210. The first support arm 206 can be hollow to accommodate the passage of electrical lines through the interior space of the first support arm and is moveable through an arc of movement 232 around the first pivot center 234.

A second pivot 220 is at an end of the first support arm 206 and is connected to a second support arm 222. The second support arm 222 is moveable through an arc of movement 224 around the second pivot center 226. A third pivot 228 is connected to an end of the second support arm 222. A third support arm 230 is connected to the third pivot 228. A red laser housing 240 is situated at the third pivot 228. A green laser housing 250 is attached to the third support arm 230 at a location along its length. The alignment of an axis GLA drawn longitudinally through the green laser housing 250 is aligned with the support arm axis SAA drawn along the longitude of the third support arm 230. A handle 252 is placed at an end 254 of a fourth support arm 251 that is attached to the green laser housing 250 and, in turn, the third support arm 230 for lateral movement of the third support arm 230 and the affixed green laser housing 250. An indicia 256 located at the third pivot 228 is provided with at least one reference point 258 for angular registration of the orientation of the third support arm 230 and the affixed green laser housing 250. In an embodiment, the indicia 256 are comprised of 360 reference points and numerical references in units of ten for an angular display of 360 degrees. Such a reference display provides for registration of the precise alignment of the third support arm 230 and the affixed green laser housing 250. In other embodiments, the reference indicia can include an electronic display of the angular alignment of the third support arm 230 and the affixed green laser housing 250, and in reference points that describe tenths of a degree of finer units.

A fifth support arm 260 is attached to the red laser housing 240 and is provided with a handle 262 at an end. The fifth support arm 260 can be used to position the red laser housing 240 relative to the ceiling mount 202 by movement of the first and second support arms and their relative pivots.

The red laser hosing is constructed and arranged with apertures 268 for the emission of red laser light. In an embodiment, the apertures 268 consist of a first longitudinal aperture 270, a central circular aperture 272 and a second longitudinal aperture 274. Likewise, the green laser hosing is constructed and arranged with apertures 278 for the emission of green laser light. In an embodiment, the apertures 278 consist of a first longitudinal aperture 280, a central circular aperture 282 and a second longitudinal aperture 284. The longitudinal apertures 270, 274, 280, 284 are for aligning anteversion of the hip. The central circular apertures 272, 282 are point lasers for reference. The operations of the emitted green and red laser light will be explained more fully below. Anteversion means rotated forwards (towards the front of the body). Each laser housing is powered by electrical cables that are threaded through the internal spaces of the structures of the various support arms and connections within the pivots themselves and a re in connection with a power source (not shown). Each laser housing 240, 250 contains one or more laser light emitters and appropriate control mechanisms for turning on and turning off the laser light emitters (not shown).

Figure 3:
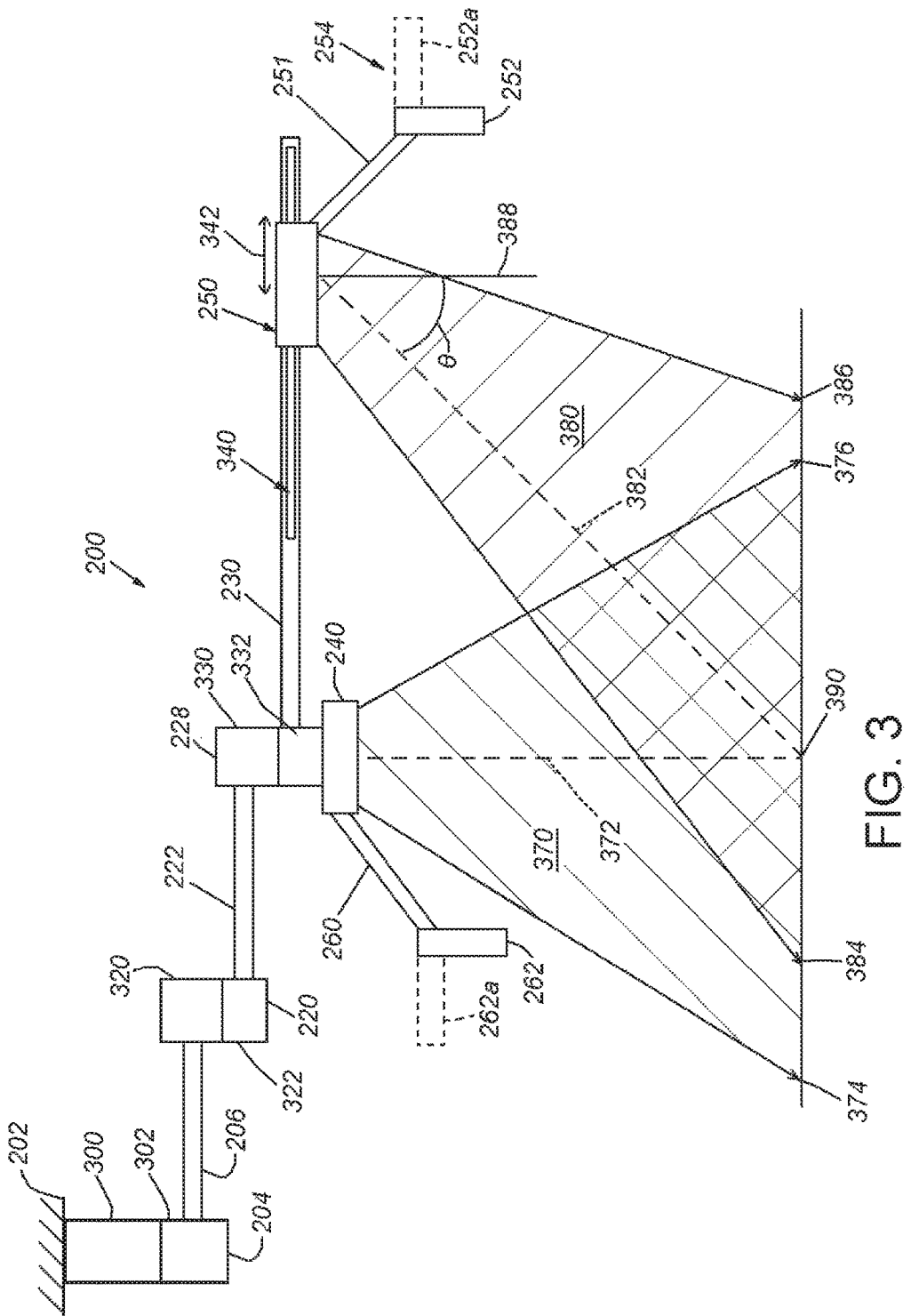
FIG. 3 is a schematic side view of a system for alignment, according to the illustrative embodiment.

FIG. 3 is a side view of the system of FIG. 2. The first pivot 204 is constructed and arranged with an upper pivot portion 300 and a lower pivot portion 302. The lower pivot portion 302 can move axially through a complete rotation relative to the upper pivot portion 300. The connection of the upper pivot portion 300 with the lower pivot portion 302 is sufficiently strong to support the attached elements that comprise the rest of the alignment system 200. Likewise, the second pivot 220 is constructed and arranged with an upper pivot portion 320 and a lower pivot portion 322. The lower pivot portion 322 can move axially through a complete rotation relative to the upper pivot portion 320.

The third pivot 228 is constructed and arranged with an upper pivot portion 330 and a lower pivot portion 332. The lower pivot portion 332 can move axially through a complete rotation relative to the upper pivot portion 330.

A lateral track 340 for movement of the green laser housing 350 such that it can be moved in a lateral motion 342 back and forth along the third support arm 230 as desired by the operator. This movement can be effected manually or by an electromechanical means (for instance, by a small electrical motor driving a power screw) that is directly or remotely operated.

Handles 252, 262 are shown oriented in a vertical oriental relative to the alignment system 200. In other embodiments, the handles 252, 262 can be oriented in horizontal configurations 252a, 262a. It is contemplated that the handles 252, 262 can be provided with swivels to provide for movement between the vertical and horizontal orientations. Handle 252 can accept a sterile light cover that is used for orientation of the green laser light housing to the acetabulum and for the anteversion of the hip.

The laser light emitted from the red laser housing 240 is depicted as the shaded area 370. A center point light beam 372 is emitted by central circular aperture 272. The longitudinal apertures 270, 274 emit the shaded area 370 in a linear field. That is to say that the emitted light is in a line from point 374 to point 376.

Likewise, the laser light emitted from the green laser housing 250 is depicted as the shaded area 380. A center point light beam 382 is emitted by central circular aperture 282. The longitudinal apertures 280, 284 emit the shaded area 380 in a linear field. That is to say that the emitted light is in a line from point 384 to point 386.

The center point light beams 372 and 382 coincide and join at an intersection point 390 that should reference the acetabulum for correcting referencing anteversion and inclination of the hip. While the red center point light beam 372 is fixed, the inclination of the green center point light beam 382 can be at a fixed angle θ relative to a vertical axis 388 or can be moveable through different angular settings, as desired by the operator.

It should be noted that, as used herein the directional terms, such as, but not limited to, "up" and "down", "upward" and "downward", "rear", "rearward" and "forward", "top" and "bottom", "inside" and "outer", "front" and "back", "inner" and "outer", "interior" and "exterior", "downward" and "upward", "upper" and "lower", "horizontal" and "vertical" should be taken as relative conventions only, rather than absolute indications of orientation or direction with respect to a direction of the force of gravity.

Figure 4:
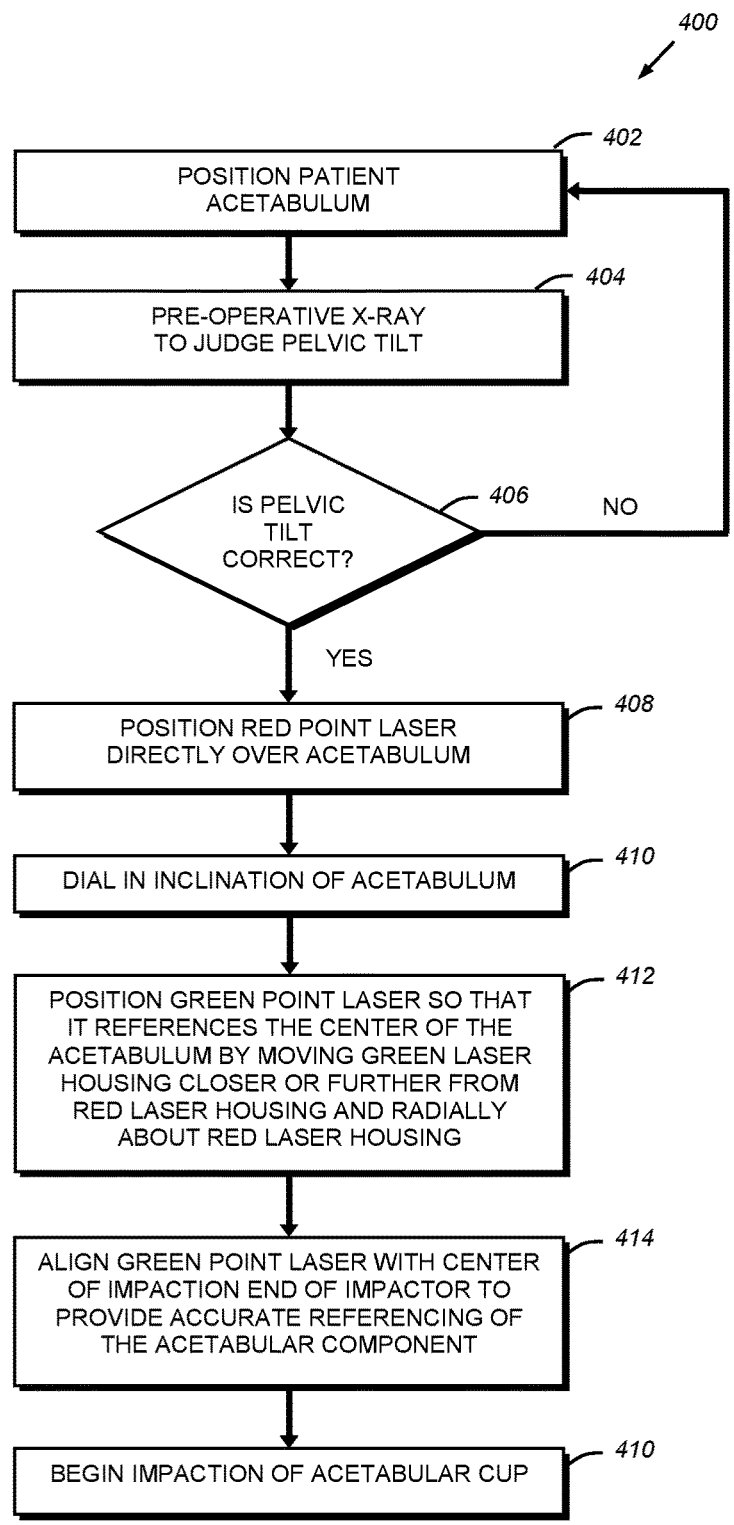
FIG. 4 is a flowchart for the employment of the system for alignment, according to the illustrative embodiment.

FIG. 4 is a flow chart depicting a method 400 of using green and red laser emitted light for alignment of the acetabulum. Although the flow chart depicts a number of blocks in numerical order, the blocks can be performed in any order. Moreover, certain blocks may be removed and/or added to the flow chart according to one or more aspects of the present disclosure.

In step 402, the patient acetabulum is positioned for the determination of proper alignment for the replacement acetabular cap. A pre-operative x-ray image is taken for evaluating and judging the pelvic tilt in step 404. The operator makes a determination in step 406 as to whether the pelvic tilt is correct. If it is not, the patient is re-positioned and a new x-ray image is taken for re-evaluation purposes. If the pelvic tilt is correct, the red laser is positioned directly over the acetabulum in step 408. This positioning involves the operator manually directing the red laser light housing 240 over the acetabulum and using the center light beam 372 to guide the final movements of the red laser light housing 240 until it is directly over the acetabulum. At this point, the inclination of the acetabulum is recorded and can be displayed visually on a nearby or remote display following a manual input or automatic input (by onboard sensors), as shown in step 410. Once the inclination of the acetabulum has been determined, the operator begins to position the green laser light so that the impactor can be properly aligned. The green laser light housing is moved closer or further from the red laser light housing 240 along its lateral track 340 and the third support arm 230 is rotated axially around the third pivot 228 so that it references the center of the acetabulum as depicted in step 412. When the center light beams 372, 382 are aligned to form intersection point 390, the proper alignment has been established and the replacement of the acetbular cup can proceed. The center of the impaction end of the impactor, that being the cup engaging element with an acetabular cup prosthesis, is aligned with the green point laser light to provide an accurate referencing of the acetabular cup prosthesis (the "acetabular cup component") as set forth in step 414. The operator then begins the impaction of the acetabular cup prosthesis into the pelvis, as shown in step 416. The precise alignment of the impactor provides for a proper alignment of the acetabular cup prosthesis and hence, a better likelihood of an efficacious outcome for the patient.

It should be clear to one of ordinary skill that the foregoing system for alignment provides for a more precise determination of the acetabular cup prosthesis by the coincidental alignment of emitted laser lights of two discrete colors.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments of the apparatus and method of the present invention, what has been described herein is merely illustrative of the application of the principles of the present invention. For example, while the lights as described above are "red" and "green" laser lights, other colors for laser lights can be substituted. For example, blue and yellow, or blue and orange, or red and blue. The emitted laser light can be viewed as a steady stream or emitted in visually observable pulses. The apparatus of the various pivots and support arms can be manipulated manually, directly through an interface or remotely, by an application. The method of alignment using the laser lights can be applied to human operators in the operating room or mechanical operators, such as a robotic medical device. It is contemplated that the coincidental alignment of the center light beams 372, 382 can be effected visually by an operator or remotely, using vision sensors and an alignment program that automatically guides the movement of the green laser light housing through its lateral and axial movements into a proper alignment. The above described alignment system and method can be applied to other surgical procedure for replacement of a cup and ball type socket, for example, to a replacement of a rotator cup. Furthermore, this alignment system and method is applicable to the veterinary field of hip replacement. Accordingly, this description is meant to be taken only by way of example, and not to otherwise limit the scope of this invention.

What is claimed is:

1. A system for an acetabular cup alignment system comprising:
    a mounting element;
    a first pivot that is provided with an upper pivot portion and a lower pivot portion, the first pivot being attached to the mounting element;
    a first support arm that is attached to the first pivot at an end, the first support arm being axially rotatable relative to the first pivot;
    a second pivot that is provided with an upper pivot portion and a lower pivot portion, the second pivot being attached to an end of the first support arm;
    a second support arm that is attached to the second pivot at an end, the second support arm being axially rotatable relative to the second pivot;
    a third pivot that is provided with an upper pivot portion and a lower pivot portion, the third pivot being attached to an end of the second support arm;
    a third support arm that is attached to the third pivot at an end, the third support arm being axially rotatable relative to the third pivot;
    a red laser housing that is provided with at least one red laser light emitter, the red laser housing being attached to the second pivot; and
    a green laser housing that is provided with at least one green laser light emitter, the green laser housing being attached to the third support arm.

2. The system as set forth in claim 1 wherein the mounting element is a ceiling mount to connect the system for an acetabular cup alignment to a ceiling.

3. The system as set forth in claim 1 wherein the red laser light housing has a handle for aligning and positioning the red laser light emitter.

4. The system as set forth in claim 1 wherein the red laser light housing has a first longitudinal aperture, a central circular aperture and a second longitudinal aperture.

5. The system as set forth in claim 4 wherein the first and second longitudinal apertures emit a linear beam of light.

6. The system as set forth in claim 4 wherein central circular light aperture emits a central point beam of light.

7. The system as set forth in claim 1 wherein the green laser light housing has a handle for aligning and positioning the green laser light emitter.

8. The system as set forth in claim 1 wherein the green laser light housing has a first longitudinal aperture, a central circular aperture and a second longitudinal aperture.

9. The system as set forth in claim 8 wherein the first and second longitudinal apertures emit a linear beam of light.

10. The system as set forth in claim 9 wherein central circular light aperture emits a central point beam of light.

11. The system as set forth in claim 1 wherein the third support arm has a track for the green laser housing that provides for lateral movement of the green laser housing.

* * * * *